United States Patent [19]
Yan

[11] Patent Number: 5,239,109
[45] Date of Patent: Aug. 24, 1993

[54] FORMATE SYNTHESIS

[75] Inventor: Tsoung Y. Yan, Philadelphia, Pa.

[73] Assignee: Mobil Oil Corporation, Fairfax, Va.

[21] Appl. No.: 808,789

[22] Filed: Dec. 16, 1991

[51] Int. Cl.⁵ .................................................. C07C 67/36
[52] U.S. Cl. ......................................................... 560/232
[58] Field of Search ........................................ 560/232

[56] References Cited

U.S. PATENT DOCUMENTS

| | | | |
|---|---|---|---|
| 4,661,623 | 4/1987 | Chang et al. | 560/232 |
| 4,661,624 | 4/1987 | Chang et al. | 560/232 |
| 4,734,525 | 3/1988 | Green | 560/232 |
| 4,790,963 | 12/1988 | Attig et al. | 560/232 X |

Primary Examiner—Arthur C. Prescott
Attorney, Agent, or Firm—Alexander J. McKillop; Malcolm D. Keen; Jessica M. Sinnott

[57] ABSTRACT

A process for making alkyl formates from a synthesis gas is described in which a synthesis gas stream is separated into a first stream and a second stream which contain CO and $H_2$. The CO and $H_2$ are reacted under high pressures to produce methanol. The CO of the second stream is reacted with water to produce formic acid. The formic acid and methanol are reacted in the presence of an alkali or alkaline earth metal catalyst such as NaOH to produce an effluent stream which includes alkyl formate and $H_2$. The $H_2$ is separated and recycled to the alcohol synthesis zone as a second source of $H_2$.

20 Claims, 1 Drawing Sheet

FORMATE SYNTHESIS

FIELD OF THE INVENTION

The invention is directed to a process for synthesizing alkyl formate from a source of hydrocarbons and oxygen, specifically a synthesis gas, in a cyclic closed loop process which includes methanol synthesis and esterification.

BACKGROUND OF THE INVENTION

Certain oxygenates such as formates are good fuel additive candidates as they have high octane properties, they can be produced from various hydrocarbon sources and can suppress pollutant emissions from vehicles. Consideration of methyl formate as a commercially viable additive for fuel blending would be favorable. Methyl formate is a good hydrocarbon fuel additive because it is an excellent gasoline blending component, having a research octane blending value, at 10 volume %, of 107 for regular gasoline and 116.5 for premium gasoline. Since formate is soluble in alcohol and ether it is a good oxygenated fuel additive and this is important since oxygenated fuels are becoming popular alternatives to hydrocarbon fuels. Other reasons why methyl formate would be a commercially desirable product are because it is colorless, flammable and agreeable in odor. However, serious attention to methyl formate as a commercially practical additive has been disfavored because of difficulties encountered in the synthesis.

U.S. Pat. No. 4,661,624 teaches synthesizing methyl formate from syngas, as a source of CO, and methanol over an alkali metal methoxide catalyst. The patent describes a solution to the pipe clogging and related manufacturing difficulties caused by a sodium methoxide catalyst precipitate which forms during methyl formate synthesis. In the described process a low product conversion is maintained so that higher concentrations of the catalyst can be used without the precipitation problem. The disadvantages of this approach include the low product conversion, an unrecycled syngas byproduct and a need to restore the supply of pure methanol. The patent also teaches maintaining a low water content in the reaction zone which is, presumably, necessary to force complete reaction of methanol to methyl formate and because sodium methoxide decomposes in water. Because syngas has a high water content, driers for the syngas are an extra expense.

U.S. Pat. No. 4,661,623 teaches a method of making methyl formate from methanol and carbon monoxide using an anionic transition metal catalyst. Described is a high pressure synthesis using concentrated anhydrous methanol. Anhydrous methanol does not contain absorbed water.

SUMMARY OF THE INVENTION

The invention is directed to a process for making alkyl formates from a synthesis gas (syngas) in which methanol synthesis is an integral part of the process. The invention utilizes a syngas stream which contains predominant amounts of CO, $H_2$ and lesser amounts of $CO_2$ and less than 20% nitrogen. The syngas is usually water saturated. The synthesis stream is separated into a first stream and a second stream. Normally, the syngas stream is simply split into two streams which both contain $H_2$. However, it would be preferable to diffuse the $H_2$ out of the second stream. Passing the stream through a palladium-type diffusion membrane would be suitable for this purpose.

The CO and $H_2$ components of the first stream are reacted under high pressures and, optionally, in the presence of a catalyst, such as a copper and/or zinc-containing catalyst, to form methanol and higher alcohols. The methanol is then contacted with the second CO stream in the presence of an alkali or alkaline earth metal catalyst and water under conditions sufficient to produce alkyl formate and $H_2$. The effluent stream produced is conveyed to a gas/liquid separator to separate $H_2$ which is recycled to the alcohol synthesis zone as a second source of $H_2$. The remaining liquid product is recovered and the formate is separated by distillation. The catalyst, water and unreacted methanol can be recovered and recycled back to the reaction zones.

DETAILED DESCRIPTION OF THE INVENTION

Figure 1:
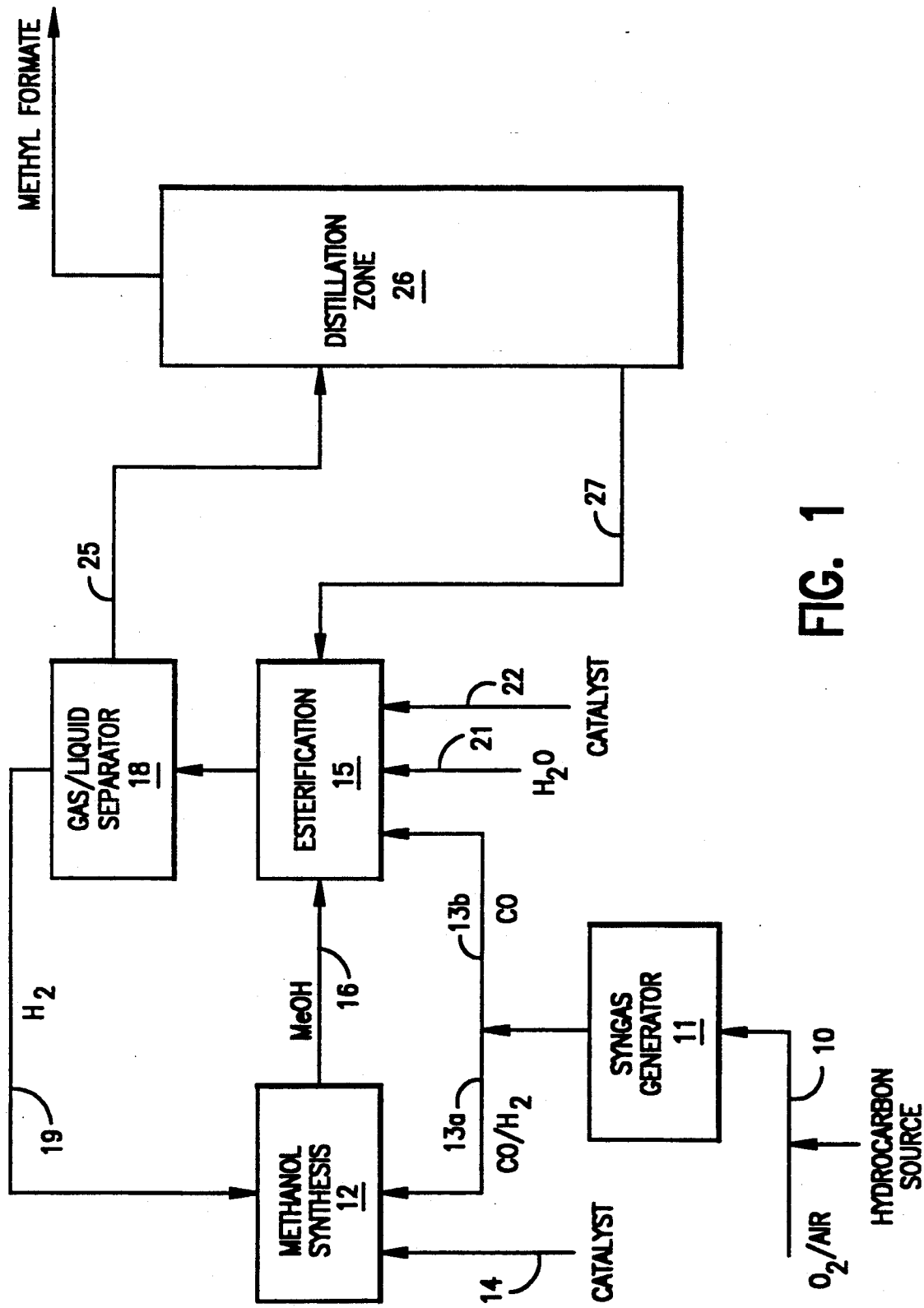
FIG. 1 is a simplified schematic flow diagram of the instant process.

The process is conducted on an efficient "closed loop" in which substantially all by-products of the reaction are recycled back through the process.

Referring to FIG. 1, a hydrocarbon source along with at least one source of oxygen such as air and pure oxygen are passed through line 10 into syngas generator 11 which produces the syngas. Preferably, the hydrocarbon source is desulfurized prior to its introduction to the syngas generator. The hydrocarbon source is coal, residual fuel oil, natural gas, naphtha or biomass.

The syngas can be made by steam reforming in which the hydrocarbons are contacted with steam or by partial oxidation in which the hydrocarbons are contacted with steam and oxygen. The syngas generator operates at pressures ranging from about 500 to 1500 psia and about 750° C. to about 900° C. Syngas preparation is the first step in many methanol synthesis procedures.

The components making up the syngas depend upon the hydrocarbon source and the method of making the syngas; however, the effluent from the syngas generator contains chiefly carbon monoxide (CO) and hydrogen ($H_2$) and low percentages of carbon dioxide ($CO_2$) and less than 2.0% nitrogen and water. The gas includes predominantly $H_2$ and CO. The molar proportions of $H_2$ to CO range from 1 to 2, preferably, 1.0 to 1.8. Contaminants such as $N_2$, $CO_2$, and $CH_3$ can be tolerated in the process but, preferably, are purged from the system to a level of less than about 10%.

The syngas stream is separated into a first process stream and a second process stream. The streams can, more or less, contain equal parts of each component and are used without further processing or purification. Preferably, however, one of the streams is passed through a palladium membrane to diffuse out the $H_2$ to enrich the CO for use in the formate synthesis. However, this is not always appropriate and can be costly. Since the presence of $H_2$ in the formate synthesis acts as a diluent, diffusing out the $H_2$ is not necessary.

The first stream is transported to an alcohol synthesis zone 12 via line 13a.

The alcohol synthesis zone operates under high pressures of 500–2000 psi, preferably 800–1500 psi and temperatures of 200° C. to 300° C., preferably 220° C. to 280° C. Various methods of methanol synthesis from syngas are known and can be adapted to the instant invention. Examples of processes include a methanol low pressure process developed by Imperial Chemical Industries in which a highly stable copper based catalyst which operates in a fixed bed reactor in a pressure range of 50 to 100 atm at 200° to 300° C. Another methanol synthesis process is described as the Lurgi Low Pressure Process in which the syngas is compressed, preheated and fed to a methanol reactor where the $H_2$, CO and $CO_2$ are reacted in the presence of a catalyst at temperatures ranging from 240° to 270° C. Another process is described as the Haldor Topsoe process in which the methanol synthesis is conducted in three radial flow converters with indirect heat exchange between the converters, the reaction pressure ranges from 1,000 to 3,000 psig. The process is a closed loop in which only part of the methanol is synthesized per pass, the remainder is recirculated to the converters along with fresh syngas. These processes are more completely described in *Hydrocarbon Processing* pp. 111 to 113 (November 1983) and "Petrochemical Handbook '91", *Hydrocarbon Processing* pp. 164 (March 1991) which are incorporated by reference in their entireties. For purposes of the instant process, fresh catalyst can be introduced into the methanol synthesis zone via line 14. Suitable catalysts include copper, chromium and zinc-containing catalysts. The alcohol produced is transported to the esterification zone 15 through line 16. Although methanol is the primary product of the alcohol synthesis, higher molecular weight alcohols can be formed such as ethanol, propanol and even higher molecular weight alcohols. These higher molecular weight alcohols can also be used to make formates.

In the esterification zone 15 alcohol, conveyed via line 16, catalyst and introduced through line 22, the second syngas stream containing CO, introduced through line 13b, from the syngas generator, react to form the desired alkyl formate product. With the aid of a base catalyst, the CO is hydrolyzed by the water present in the system to form the formic (carboxylic) acid. The reaction mechanism is as follows:

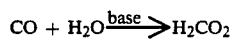

Additional water for the hydrolysis enters the reaction zone through line 21. A base is used to promote the reaction. Suitable bases include the alkali or alkaline earth metal hydroxides, oxides or carbonates examples of which include NaOH, KOH, LiOH, $K_2CO_3$ and $Na_2CO_3$ which are soluble in water. Fresh catalyst is introduced to the reaction via line 22. A slight catalyst purge can be used to maintain catalytic activity in the esterification zone. The carboxylic acid forming reaction consumes water. Stoichiometrically, 1 mole of water is required for each mole of CO. Excess water is desirable for hydrolysis; however, excess water is undesirable for ester (formate) formation. Thus, a suitable amount of water is in the range of 0.01 to 10 moles $H_2O$/mole CO. The molar amount of methanol to CO ranges from about 0.1 to 10 and the molar amount of $H_2O$ to methanol ranges from about 0.01 to 10.

Preferably within the same reactor, although a separate reactor can be used to carry-out this step, the carboxylic acid and the alcohol react to form the ester: alkyl formate. This reaction is also conducted in the presence of the alkali or alkaline earth metal catalyst which enters the reactor through line 22. The catalyst is, preferably, the same as the alkali or alkaline earth metal base which promotes the formic acid reaction. The formic acid and methanol conveyed via line 16 undergo esterification to form the desired alkyl formate. The water of reaction is consumed in the hydration step. The reaction mechanism is as follows:

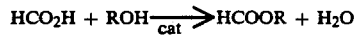

wherein R is a low molecular weight alkyl group such as methyl, ethyl or propyl.

If the esterification reaction is conducted in a separate reactor, the water can be removed and recycled for the carboxylic acid synthesis. The esterification process conditions are detailed in Table 1.

TABLE 1

| CONDITIONS | BROAD | PREFERRED |
|---|---|---|
| Temp., °C. | 0–300 | 20–200 |
| Pressure, psia | 0–2000 | 10–500 |
| LHSV | 0.01–50 | 0.1–10 |
| Catalyst, conc. (mole %) | 0.001–6 | 0.1–2 |

The esterification reactor can be a stirred tank reactor or a fixed bed reactor with liquid recycle.

The effluent stream containing alkyl formate, $H_2$, catalyst, unconsumed water, if any, and methanol is withdrawn from the top of the esterification zone 15 and passed through gas/liquid separator 18 via line 17. A $H_2$-rich recycle gas is withdrawn from the top of the separator and conveyed to the methanol synthesis zone via line 19. A formate-rich stream is conveyed through line 25 to distillation zone 26.

Distillation is necessary for the most efficient process operation because it integrates separation of the desired product from the materials which can be recycled back into the process. Recycle materials include $H_2$, water, methanol, esterification catalyst as well as the alkali or alkaline earth metal catalyst. Any of these recycle components are recycled back to the esterification zone 15 through line 27. In this manner the process is essentially a closed-loop, self-contained reaction which utilizes the by-products of reaction and conserves the energy of reaction.

The alkyl formate product is recovered from the top of the distillation zone for use as a fuel blending component for liquid hydrocarbon fuels, liquid oxygenated fuels or a combination thereof.

The methyl formate synthesized as described herein would be a commercially practical fuel blending component. Methyl formate is colorless, flammable and agreeable in odor. It is saponified by water or alkaline solutions and is soluble in alcohol and ether. Its solubility in water is 30 g/100 g, specific gravity is 0.950–0.980 (20°/20° C.); the melting point is −99.8° C., the boiling point is 31.8° C., flash point is −25.6° F., weight/gal. 8.03 lbs (68° F.); refractive index is 1.3431 (20° C.) and explosive limits in air range from 4.5 to 23% by volume. Methyl formate contains 2 oxygen atoms per molecule with an oxygen content of 53.3% (vs. 18.2% for methyl-tert-butyl-ether). Thus, the use of methyl formate as a blending component will enable gasolines to meet mandated oxygen contents.

What is claimed is:

1. A process for making alkyl formate from a hydrocarbon source comprising:

preparing a fluid stream, characterized by the presence of major amounts of CO and $H_2$ from the hydrocarbon source and at least one source of oxygen;

separating the fluid stream into a first stream and a second stream;

conveying the first stream to an alcohol synthesis zone to synthesize a mixture of low molecular weight alcohols by reacting the CO and $H_2$ under alcohol synthesis conditions;

conveying the second stream to an esterification zone to form formic acid by contacting the CO in the second stream and water over a basic alkali or alkaline earth metal catalyst consisting of NaOH, KOH, LiOH, $K_2CO_3$ and $Na_2CO_3$;

conveying the low molecular weight alcohols to the esterification zone; and synthesizing alkyl formate by reacting the formic acid and the low molecular weight alcohols in the presence of the basic alkali or alkaline earth metal catalyst consisting of NaOH, KOH, LiOH, $K_2CO_3$ and $Na_2CO_3$ under conditions sufficient to produce alkyl formate and $H_2$; the conditions include temperatures ranging from 0° to 300° C., pressures of 0 to 2000 psia, LHSV of 0.01 to 50 and catalyst concentration in mole % of 0.001 to 6.

2. The process of claim 1 in which the alkyl formate is separated by distillation.

3. The process of claim 1 in which the first stream includes CO and $H_2$ and the second stream includes CO and is free of $H_2$.

4. The process of claim 3 in which the second stream is passed through a palladium diffuser to separate the $H_2$.

5. The process as described in claim 4 which includes adding the separated $H_2$ to the alcohol synthesis zone as a second source of $H_2$.

6. The process of claim 1 in which the alcohol synthesis conditions include pressures ranging from 500 psi to 2000 psi, the presence of a copper, chromium or zinc catalyst and temperatures ranging from 200° to 300° C.

7. The process of claim 1 in which the conditions sufficient to produce the alkyl formate include temperatures ranging from 20° to 200° C., pressures of 10 to 500 psia, LHSV ranging from 0.1 to 10 and catalyst concentration ranging from 0.1 to 2.

8. The process of claim 1 in which the low molecular weight alcohols include a major proportion of methanol.

9. A process for the production of alkyl formate from a synthesis gas comprising:

feeding a light hydrocarbon stream and at least one source of oxygen into a synthesis gas generator to produce a fluid stream containing CO and $H_2$;

separating the fluid stream into a first stream and a second stream;

reacting the CO and $H_2$ of the first stream under alcohol synthesis conditions in an alcohol synthesis zone to produce a low molecular weight alcohol;

contacting the second stream with water and an alkali or alkaline earth metal catalyst consisting of NaOH, KOH, LiOH, $K_2CO_3$ and $Na_2CO_3$ to produce a process stream containing formic acid;

reacting the formic acid with the low molecular weight alcohol over the alkali or alkaline earth metal catalyst consisting of NaOH, KOH, LiOH, $K_2CO_3$ and $Na_2CO_3$ in an esterification zone under conditions sufficient to produce alkyl formate and $H_2$; the conditions include temperatures ranging from 0° to 300° C., pressures from 0 to 2000 psia, LHSV of 0.01 to 50 and catalyst concentration ranging from 0.001 to 6 mole %.

separating the $H_2$; and recycling the $H_2$ to the alcohol synthesis zone whereby the recycled $H_2$ provides an additional source of $H_2$ for the alcohol synthesis.

10. The process of claim 9 in which the first stream includes CO and $H_2$ and the second stream includes CO and is free of $H_2$.

11. The process of claim 9 in which the alcohol synthesis conditions include pressures ranging from 500 psi to 2000 psi, the presence of a copper, chromium or zinc catalyst and temperatures ranging from 200° to 300° C.

12. The process of claim 9 in which the conditions sufficient to produce the alkyl formate include temperatures ranging from 20° to 200° C., pressures of 10 to 500 psia, LHSV ranging from 0.1 to 10 and catalyst concentration ranging from 0.1 to 2.

13. The process of claim 9 in which the low molecular weight alcohol is methanol.

14. The process of claim 9 which additionally comprises blending a minor amount of the alkyl formate into a fuel which is a hydrocarbon fuel or oxygenated fuel or a combination thereof.

15. A process for making alkyl formate from a synthesis gas comprising the steps of separating the synthesis gas into a first stream and a second stream;

synthesizing methanol from the first stream and a source of $H_2$ in a methanol synthesis zone;

contacting CO of the second stream with water in the presence of NaOH to produce formic acid;

reacting the formic acid with the methanol over the NaOH in an esterification zone under conditions sufficient to produce alkyl formate and $H_2$; the conditions include temperatures ranging from 0° to 300° C., pressures ranging from 0 to 2000 psia, LHSV ranging from 0.1 to 10 and catalyst concentration of 0.1 to 2;

separating the $H_2$; and recycling the separated $H_2$ to the alcohol synthesis zone.

16. The process of claim 15 in which the first stream contains at least one component which is CO and the second stream contains at least one component which is CO and is free of $H_2$.

17. The process of claim 15 in which the alcohol synthesis conditions include pressures ranging from 500 psi to 2000 psi, the presence of a copper, chromium or zinc catalyst and temperatures ranging from 200° to 300° C.

18. The process of claim 16 in which the conditions sufficient to produce the alkyl formate include temperatures ranging from 20° to 200° C., pressures from 10 to 500 psia, LHSV of 0.1 to 10 and catalyst concentration ranging from 0.1 to 2.

19. The process of claim 16 in which the low molecular weight alcohol is methanol.

20. The process of claim 16 which further comprises blending a minor amount of the alkyl formate into a fuel which is a hydrocarbon fuel, oxygenated fuel or a combination thereof.

* * * * *